(12) United States Patent
Levijoki et al.

(10) Patent No.: US 11,433,021 B2
(45) Date of Patent: Sep. 6, 2022

(54) PALONOSETRON FOR THE TREATMENT OR PREVENTION OF NAUSEA AND VOMITING

(71) Applicant: ORION CORPORATION, Espoo (FI)

(72) Inventors: Jouko Levijoki, Helsinki (FI); Sari Pappinen, Raisio (FI); Lasse Saloranta, Sauvo (FI)

(73) Assignee: ORION CORPORATION, Espoo (FI)

( * ) Notice: Subject to any disclaimer, the term of this patent is extended or adjusted under 35 U.S.C. 154(b) by 0 days.

(21) Appl. No.: 16/961,017

(22) PCT Filed: Jan. 11, 2019

(86) PCT No.: PCT/FI2019/050017
§ 371 (c)(1),
(2) Date: Jul. 9, 2020

(87) PCT Pub. No.: WO2019/138162
PCT Pub. Date: Jul. 18, 2019

(65) Prior Publication Data
US 2020/0345632 A1 Nov. 5, 2020

(30) Foreign Application Priority Data

Jan. 12, 2018 (FI) .................................. 20185035

(51) Int. Cl.
| | | |
|---|---|---|
| *A61K 47/02* | (2006.01) | |
| *A61K 9/00* | (2006.01) | |
| *A61K 31/473* | (2006.01) | |
| *A61K 47/10* | (2017.01) | |
| *A61K 47/32* | (2006.01) | |
| *A61K 47/34* | (2017.01) | |
| *A61K 47/38* | (2006.01) | |
| *A61K 47/40* | (2006.01) | |

(52) U.S. Cl.
CPC .......... *A61K 9/0048* (2013.01); *A61K 31/473* (2013.01); *A61K 47/02* (2013.01); *A61K 47/10* (2013.01); *A61K 47/32* (2013.01); *A61K 47/34* (2013.01); *A61K 47/38* (2013.01); *A61K 47/40* (2013.01)

(58) Field of Classification Search
CPC ........ A61K 47/02; A61K 47/10; A61K 47/32; A61K 47/34; A61K 47/38; A61K 47/40; A61K 31/473; A61K 9/048; A61P 1/08; A61P 43/00
See application file for complete search history.

(56) References Cited

U.S. PATENT DOCUMENTS

| 7,947,724 B2 * | 5/2011 | Calderari ........... A61K 31/4747 |
| | | 514/397 |
| 2013/0231315 A1 * | 9/2013 | Fadini .................. A61K 31/473 |
| | | 514/171 |

FOREIGN PATENT DOCUMENTS

| CN | 103845295 A * | 6/2014 |
| WO | WO 2004/073714 A1 | 9/2004 |
| WO | WO 2014/018932 A2 | 1/2014 |
| WO | WO 2015/044504 A1 | 4/2015 |

OTHER PUBLICATIONS

Xiao Hu et al.: "Higher dose of palonosetron versus lower dose of palonosetron plus droperidol to prevent postoperative nausea and vomiting after eye enucleation and orbital hydroxyapatite implant surgery: a randomized, double-blind trial", *Drug Design, Development and Therapy*, vol. 11, (2017), pp. 1465-1472.
Jan Nyrop Jakobsen et al.: "Prevention of chemotherapy-induced nausea and vomiting in elderly cancer patients", *Critical Reviews in Oncology/Hematology*, vol. 71, No. 3, (2009), pp. 214-221.
International Search Report, issued in corresponding International Application No. PCT/FI2019/050017 from the European Patent Office, dated Mar. 27, 2019, 3 pages.

* cited by examiner

*Primary Examiner* — Ali Soroush

(74) *Attorney, Agent, or Firm* — Birch, Stewart, Kolasch & Birch, LLP

(57) ABSTRACT

The invention relates to a method for treating or preventing nausea and vomiting. The method comprises administering an eye drop composition comprising palonosetron or a pharmaceutically acceptable salt thereof to the eye of the subject. The ocular administration results in fast systemic absorption, improved bioavailability compared to oral route and extended elimination time.

13 Claims, 2 Drawing Sheets

PALONOSETRON FOR THE TREATMENT OR PREVENTION OF NAUSEA AND VOMITING

This is a National Stage Application under 35 U.S.C. § 371 of International Patent Application No. PCT/FI2019/050017, filed Jan. 11, 2019, which claims the benefit of priority of Finnish Patent Application No. 20185035, filed Jan. 12, 2018, both of which are incorporated herein by reference.

TECHNICAL FIELD

The present invention relates to a method for treating or preventing nausea and vomiting in a subject. The method comprises administering to the eye of the subject an effective amount of an eye drop composition comprising palonosetron or a pharmaceutically acceptable salt thereof. The present invention also relates to the eye drop compositions useful in the method.

BACKGROUND OF THE INVENTION

Nausea and vomiting are very common symptoms and can be caused by wide range of factors. Nausea and vomiting are common side effects of radiotherapy and chemotherapy of malignant tumors thereby seriously affecting the quality of life of patients. Therefore, the prevention or treatment of chemotherapy-induced nausea and vomiting (CINV) and radiotherapy-induced nausea and vomiting (RINV) have become an important part of the comprehensive treatment of cancer. Other conditions involving nausea and vomiting include, for example, post-operative nausea and vomiting (POVN) and motion sickness (e.g. travel sickness, car sickness and seasickness). Several 5-$HT_3$ antagonists have been developed for use in inhibiting nausea and vomiting. Drugs within this class include, for example, granisetron, ondansetron, dolasetron, tropisetron and palonosetron. These 5-$HT_3$ antagonists are administered mainly intravenously or orally. Intravenous administration is inconvenient and needs to be given by a nurse with professional skills. Oral administration of 5-$HT_3$ antagonists is associated with drawbacks such as difficult dosing due to vomiting, low bioavailability and slow onset of action.

Thus, there is a need for more convenient and practical dosage form of 5-$HT_3$ antagonists for patients in need of quick and easy medication which still provide rapid onset of action, good bioavailability and reliable dosing accuracy.

SUMMARY OF THE INVENTION

It has been found that palonosetron or a pharmaceutically acceptable salt thereof is particularly suitable for ocular administration resulting in rapid and long-term amelioration of nausea and vomiting due to fast systemic absorption, improved bioavailability compared to oral route and extended elimination time. The eye drop compositions according to the invention provide therapeutic effect by non-invasive route of administration without the need for hospital setting thereby increasing patient compliance to the treatment. Eye drops are easy to administer by the patient at home and do not cause ocular discomfort. Therefore, the present invention provides a significant improvement in the treatment and prevention of nausea and vomiting.

Thus, according to one embodiment of the invention, the present invention provides a method for the treatment or prevention of nausea and vomiting in a subject comprising administering to the eye of the subject in need thereof an effective amount of an eye drop composition comprising palonosetron or a pharmaceutically acceptable salt thereof.

According to another embodiment of the invention, the present invention provides an eye drop composition comprising palonosetron or a pharmaceutically acceptable salt thereof as an active ingredient.

According to another embodiment of the invention, the present invention provides an eye drop composition comprising palonosetron or a pharmaceutically acceptable salt thereof as an active ingredient for use in the treatment or prevention of nausea and vomiting.

According to another embodiment of the invention, the present invention provides the use of an eye drop composition comprising palonosetron or a pharmaceutically acceptable salt thereof as an active ingredient in the manufacture of a medicament for the treatment or prevention of nausea and vomiting.

According to one embodiment of the invention the subject to be treated is human. According to other embodiment of the invention the subject to be treated is animal, particularly a companion animal such as a dog or a cat.

According to one embodiment of the invention, the present invention provides a medicinal kit comprising a) an eye drop composition comprising palonosetron or a pharmaceutically acceptable salt thereof as an active ingredient, b) a package for containing said composition, and c) instructions for administering said composition on the eye of a patient for the treatment or prevention of nausea and vomiting.

DETAILED DESCRIPTION OF THE INVENTION

Figure 1:
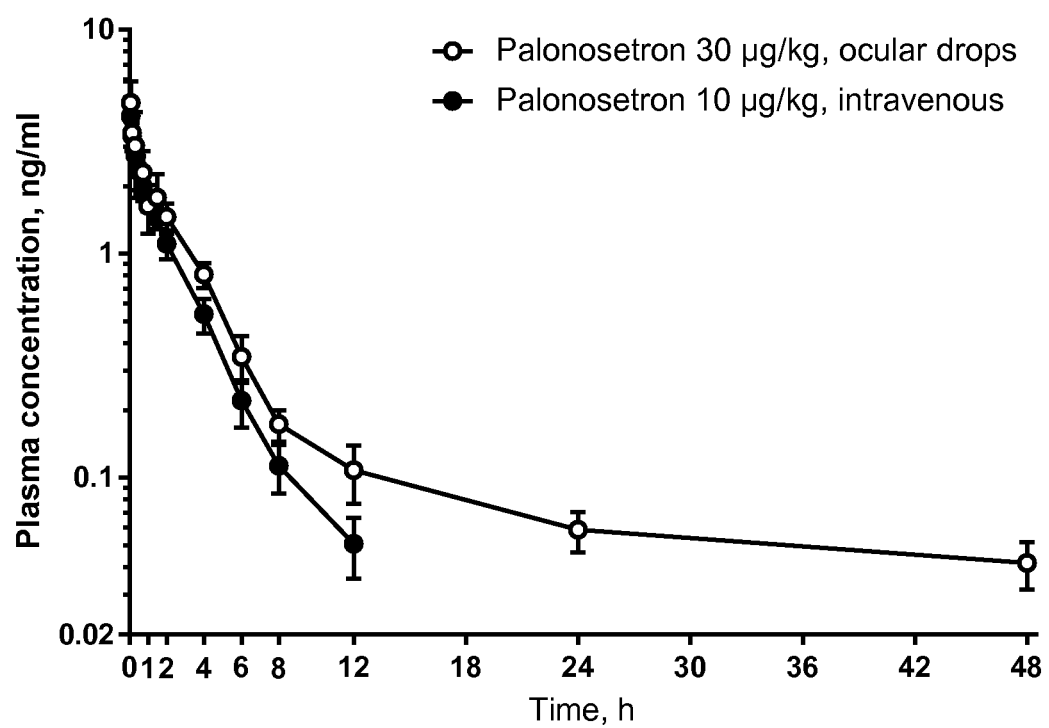
FIG. 1 shows palonosetron plasma concentrations in systemic circulation after 30 µg/kg palonosetron ocular drops compared to 10 µg/kg intravenous palonosetron administration in Beagle dogs (n=6). Shown are mean±SD.

The term "nausea", as used herein, refers to a sensation of unease and discomfort in the upper stomach with an involuntary urge to vomit. The term "vomiting" refers to expulsion of stomach contents including retching (vomiting movements without expulsion of matter).

The term "administration to the eye", as used herein, refers to applying topically to the eye and surrounding tissues, particularly to the inner surface of the eye and the inner surface of the eyelids (including e.g. cornea, conjunctiva and sclera). The term includes, for example, instillation administration, administration into conjunctival sac and conjunctival administration.

The term "eye drop composition", as used herein, refers to a liquid or semisolid pharmaceutical composition adapted to administration to the eye. Typical example of an eye drop composition is an ophthalmic aqueous solution to be administered dropwise to the eye.

The term "subject" refers to a mammal including human.

The present invention relates to a method for the treatment or prevention of nausea and vomiting in a subject comprising administering to the eye of the subject in need thereof an effective amount of an eye drop composition comprising palonosetron or a pharmaceutically acceptable salt thereof as the active ingredient.

According to one particular aspect of the invention, the present invention provides a method for the treatment or prevention of nausea and vomiting associated with cancer treatment in humans, including chemotherapy-induced nausea and vomiting (CINV) and radiotherapy-induced nausea and vomiting (RINV).

According to another particular aspect of the invention, the present invention provides a method for the treatment or prevention of nausea and vomiting associated motion sickness such as travel sickness or car sickness in animals, particularly in companion animals such as a dog or a cat.

The amount of palonosetron or a pharmaceutically acceptable salt thereof to be administered is suitably selected such as to provide sufficient nausea and vomiting inhibiting effect. Accordingly, for the treatment or prevention of nausea and vomiting in humans, for example associated with CINV, RINV or POVN, palonosetron or a pharmaceutically acceptable salt thereof, preferably hydrochloride salt, is administered to the eye generally in an amount of 0.3-300 μg/kg, preferably 0.5-200 μg/kg, more preferably 1-100 μg/kg, and typically 5-50 μg/kg. For the treatment or prevention of nausea and vomiting in animals, particularly companion animals such as dogs or cats, for example associated with motion sickness, palonosetron or a pharmaceutically acceptable salt thereof, preferably hydrochloride salt, is administered to the eye generally in an amount of 0.3-1000 μg/kg, preferably 0.5-500 μg/kg, more preferably 1-300 μg/kg, and typically 3-120 μg/kg.

The actual amount of the drug to be administered may depend on numerous factors, such as the species, age and weight of the subject to be treated, the active ingredient used, and the type of the composition.

According to one embodiment of the invention, the eye drop composition according to the invention comprises palonosetron or a pharmaceutically acceptable salt thereof as a sole active ingredient.

According to one other embodiment of the invention, the eye drop composition according to the invention may comprise in addition to palonosetron or a pharmaceutically acceptable salt thereof one or more other active ingredient(s) useful in the treatment or prevention of nausea and vomiting or related conditions and suitable for providing systemic effect by ocular administration.

Palonosetron or a pharmaceutically acceptable salt thereof can be formulated into a dosage form adapted for administration to the eye by combining the drug substance with conventional pharmaceutical diluents and carriers commonly used in eye drop compositions. The eye drop composition useful in the method of the invention may be, for example, in a liquid or semisolid form such as in the form of a solution, emulsion or suspension.

Preferably, the eye drop composition is in the form of an aqueous solution adapted for administration to the eye of the subject. The concentration of palonosetron or a pharmaceutically acceptable salt thereof in the eye drop composition, e.g. in the aqueous solution composition, is generally within the range of about 0.001 to about 10% (w/w), typically from about 0.01 to about 5% (w/w), preferably from about 0.05-3% (w/w), more preferably from about 0.1 to about 2% (w/w), per weight of the composition. According to one further embodiment, the concentration of palonosetron or a pharmaceutically acceptable salt thereof in the eye drop composition, e.g. in the aqueous solution composition, is within the range of from about 0.01 to about 1% (w/w), from about 0.05-0.5% (w/w), or from about 0.1 to about 0.4% (w/w), per weight of the composition.

The preferred salt of palonosetron is hydrochloride salt.

According to one embodiment, the eye drop composition comprises about 0.01-5%, preferably about 0.05-3%, more preferably from about 0.1 to about 2%, per weight of the composition, of palonosetron or a pharmaceutically acceptable salt thereof, and about 70-99%, preferably about 75-98%, for example about 80-97%, per weight of the composition, of sterile water. According to one further embodiment, the eye drop composition comprises 0.01-1%, 0.05-0.5%, or from about 0.1 to about 0.4%, per weight of the composition, of palonosetron or a pharmaceutically acceptable salt thereof, and at least 90%, preferably at least 95%, per weight of the composition, of sterile water.

The composition may additionally comprise a tonicity adjusting agent such as sodium chloride or mannitol, pH adjusting agents or buffering agents such as sodium hydroxide, hydrochloric acid, citric acid/sodium citrate, tartaric acid, fumaric acid, antioxidants such as butylated hydroxyanisole (BHA) or butylated hydroxytoluene (BHT), chelating agents such as edetate disodium, thickening agents such as polyvinylpyrrolidone (povidone), polyvinyl alcohol, polyethylene glycol, polyacrylic acid or a cellulose derivative such as sodium carboxymethylcellulose, chelating agents such as disodium edetate and other ingredients commonly used in the preparation of eye drop compositions.

Suitably, the eye drop composition may comprise about 0.1-10%, preferably about 0.5-5%, per weight of the composition, of a tonicity adjusting agent such as sodium chloride or mannitol. Sodium chloride can be suitably used in an amount of about 0.1-2%, preferably about 0.1-1%, per weight of the composition. Mannitol can be suitably used in an amount of about 1-10%, preferably about 2-5%, per weight of the composition. The osmolality of the eye drop composition is suitably adjusted to 200-600 mOsm/kg, preferably to about 300 mOsm/kg. In some embodiments, the eye drop composition comprises 0.5-2%, per weight of the composition, of a tonicity adjusting agent such as sodium chloride.

The eye drop composition may also suitably comprise about 0.1-5%, preferably about 0.5-3%, per weight of the composition, of a thickening agent such as polyvinylpyrrolidone.

The eye drop composition may also suitably comprise about 0.05-5%, preferably about 0.1-2%, for example about 0.2-1%, per weight of the composition, of buffering agent such as citric acid/sodium citrate.

The pH of the eye drop composition is generally within the range of from about 3 to about 8.5, preferably from about 3.5 to about 7.0, more preferably from about 4.0 to about 6.0.

According to one embodiment, the eye drop composition comprises ion-pairing agents such as hyaluronic acid or glucuronic acid. The eye drop composition may comprise about 0.1-5%, preferably about 0.5-10%, per weight of the composition, of ion-pairing agents such as hyaluronic acid or glucuronic acid.

According to an particularly preferred embodiment, the eye drop composition comprises complexing agents such as cyclodextrins. The term "cyclodextrin" refers to a cyclic dextrin molecule that is formed by enzyme conversion of starch. Various cyclodextrins are commercially available including hydroxypropyl-β-cyclodextrin, hydroxypropyl-γ-cyclodextrin, sulfobutylether-β-cyclodextrin and γ-cyclodextrin.

It was found that cyclodextrins, particularly hydroxypropyl-β-cyclodextrin, hydroxypropyl-γ-cyclodextrin and sulfobutylether-β-cyclodextrin, were able to significantly improve local tolerance of the eye drop composition, in particular in decreasing signs of milder discomfort of the eye such as blepharospasm and itching. The eye drop composition suitably comprises about 0.5-25%, preferably about 1-20%, more preferably about 2-15%, for example about 3-12%, per weight of the composition, of cyclodextrin. Hydroxypropyl-β-cyclodextrin, hydroxypropyl-γ-cyclodextrin and sulfobutylether-β-cyclodextrin are particularly preferred.

According to one embodiment, the eye drop composition comprises
(a) 0.01-5%, preferably about 0.05-3%, more preferably from about 0.1 to about 2%, per weight of the composition, of palonosetron or a pharmaceutically acceptable salt thereof;
(b) 0.5-25%, preferably about 1-20%, more preferably about 2-15%, for example about 3-12%, per weight of the composition, of cyclodextrin;
(c) 0.1-10%, preferably about 0.5-5%, per weight of the composition, of a tonicity adjusting agent;
(d) 0.05-5%, preferably about 0.1-2%, for example about 0.2-1%, per weight of the composition, of buffering agent; and
(e) 70-99%, preferably about 75-98%, for example about 80-97%, per weight of the composition, of sterile water.

According to another embodiment, the eye drop composition comprises
(a) 0.01-5%, per weight of the composition, of palonosetron or a pharmaceutically acceptable salt thereof;
(b) 0.5-25%, per weight of the composition, of cyclodextrin;
(c) 0.1-10%, per weight of the composition, of a tonicity adjusting agent;
(d) 0.05-5%, per weight of the composition, of buffering agent; and
(e) 70-99%, per weight of the composition, of sterile water.

According to still another embodiment, the eye drop composition comprises
(a) about 0.05-3%, per weight of the composition, of palonosetron or a pharmaceutically acceptable salt thereof;
(b) about 1-20%, per weight of the composition, of cyclodextrin;
(c) about 0.5-5%, per weight of the composition, of a tonicity adjusting agent;
(d) about 0.1-2%, per weight of the composition, of buffering agent; and
(e) about 75-98%, per weight of the composition, of sterile water.

According to still another embodiment, the eye drop composition comprises
(a) about 0.1-2%, per weight of the composition, of palonosetron or a pharmaceutically acceptable salt thereof;
(b) about 3-12%, per weight of the composition, of cyclodextrin;
(c) about 0.5-5%, per weight of the composition, of a tonicity adjusting agent;
(d) about 0.2-1%, per weight of the composition, of buffering agent; and
(e) about 80-97%, per weight of the composition, of sterile water.

According to still another embodiment of the invention, eye drop composition comprises
(a) about 0.1-2%, per weight of the composition, of palonosetron or a pharmaceutically acceptable salt thereof;
(b) about 2-15%, per weight of the composition, of cyclodextrin selected from hydroxypropyl-β-cyclodextrin, hydroxypropyl-γ-cyclodextrin and sulfobutylether-β-cyclodextrin;
(c) about 1-10%, per weight of the composition, of mannitol;
(d) about 0.2-1%, per weight of the composition, of a buffering agent which is citric acid/sodium citrate; and
(e) about 80-97%, per weight of the composition, of sterile water.

The eye drop formulation can be prepared e.g. by dissolving the active ingredient and excipients to the vehicle, for example water, followed by pH adjustment, if necessary, and sterile filtering.

The eye drop composition is preferably given to the eye of the subject from a prefilled bottle, ampoule or pipette in a volume ranging typically from about 0.01 to about 0.3 ml, more preferably from about 0.015 to about 0.2 ml, for example from about 0.02 to about 0.15 ml, of the eye drop composition.

Preferably, said package is an applicator, e.g. a squeezable prefilled single-use bottle, ampoule or pipette capable of dosing fixed volumes of the eye drop composition. The squeezable bottle, ampoule or pipette is preferably prepared form polymer material, such as LDPE. Suitably, the volume of the suitable bottle, ampoule or pipette ranges from about 0.5 to 5 ml. For example, about 0.5 to about 2 ml of the eye drop composition can be filled into single use blow fill seal (BFS) LDPE ampoules having volume of 0.5 ml, 1 ml or 2 ml.

The composition can be provided in the form of medicinal kit comprising a) an eye drop composition comprising palonosetron or a pharmaceutically acceptable salt thereof as an active ingredient, b) a package for containing said composition, and c) instructions for administering said composition on the eye of a patient for the treatment or prevention of nausea and vomiting.

In situations where treatment or prevention of nausea and vomiting is desired, suitable amount of the eye drop composition comprising palonosetron or a pharmaceutically acceptable salt thereof is administered to one or both eyes of the subject. The composition is given according to the need of the subject, for example daily or several times a day.

The invention is further illustrated by the following examples, which are not meant to limit the scope of the invention.

Formulation Example 1

| | |
|---|---|
| Palonosetron hydrochloride | 3.38 mg (equivalent to 3 mg of palonosetron base) |
| Povidone K30 | 20 mg |
| Sodium hydroxide | to adjust to pH 4.8 |
| Sodium chloride (0.9%) | ad 1 ml |

Formulation Example 2

| Palonosetron hydrochloride | 5.64 mg (equivalent to 5 mg of palonosetron base) |
|---|---|
| Povidone K30 | 10 mg |
| Sodium chloride (0.9%) | ad 1 ml |
| | pH 6.1 |

Formulation Example 3

| Palonosetron hydrochloride | 3.38 or 6.76 mg (equivalent to 3 or 6 mg of palonosetron base) |
|---|---|
| Hydroxypropyl-β-cyclodextrin | 100 mg |
| Mannitol | 25 mg |
| Citrate buffer pH 4.8 | ad 1 ml |

Citrate buffer pH 4.8 was prepared in this and the following examples as follows:

| Citric acid monohydrate | 168.0 mg |
|---|---|
| Sodium citrate | 353 mg |
| Sterile water | ad 100 ml |

Citric acid and sodium citrate is dissolved into the water. pH of solution is adjusted to pH 4.8 with 1M NaOH or 1M HCl, if needed.

Formulation Example 4

| Palonosetron hydrochloride | 3.38 mg (equivalent to 3 mg of palonosetron base) |
|---|---|
| Hydroxypropyl-β-cyclodextrin | 50 mg |
| Mannitol | 35 mg |
| Citrate buffer pH 4.8 | ad 1 ml |

Formulation Example 5

| Palonosetron hydrochloride | 3.38 mg (equivalent to 3 mg of palonosetron base) |
|---|---|
| Sulfobutylether-β-cyclodextrin | 100 mg |
| Mannitol | 25 mg |
| Citrate buffer pH 4.8 | ad 1 ml |

Formulation Example 6

| Palonosetron hydrochloride | 3.38 or 6.76 mg (equivalent to 3 or 6 mg of palonosetron base) |
|---|---|
| Hydroxypropyl-γ-cyclodextrin | 100 mg |
| Mannitol | 25 mg |
| Citrate buffer pH 4.8 | ad 1 ml |

Formulation Example 7

| Palonosetron hydrochloride | 3.38 mg (equivalent to 3 mg of palonosetron base) |
|---|---|
| γ-cyclodextrin | 100 mg |
| Mannitol | 25 mg |
| Citrate buffer pH 4.8 | ad 1 ml |

Formulation Example 8

| Palonosetron hydrochloride | 3.38 mg (equivalent to 3 mg of palonosetron base) |
|---|---|
| Hyaluronic acid 12 kDa | 10 mg |
| Mannitol | 50 mg |
| Citrate buffer pH 4.8 | ad 1 ml |

Formulation Example 9

| Palonosetron hydrochloride | 3.38 mg (equivalent to 3 mg of palonosetron base) |
|---|---|
| Glucuronic acid | 30 mg |
| Citrate buffer pH 4.8 | ad 1 ml |

The above formulations can be prepared by dissolving the excipients and drug substance in the carrier solution followed by sterilized filtration.

Experiment 1. Bioavailability of Palonosetron as Ocular Drops Vs. Intravenous Administration Methods:

Bioavailability of palonosetron as ocular drops at the dose of 30 µg/kg was compared to 10 µg/kg intravenous (i.v.) palonosetron in Beagle dogs (n=6). The study was a crossover study with 7 days washout period between the treatment periods. The animals were fasted overnight before dosing by withdrawing the remaining feed (if any) at least 12 h before dosing. On dosing days food was offered approximately at 4 h after dosing (after the 4 h blood sampling).

Palonosetron 30 µg/kg eye drops prepared according to Formulation Example 1 were administered in the eye using a micropipette in an amount of 10 µl/kg (approximately half volume in each eye).

Palonosetron 10 µg/kg intravenous dose was administered in cephalic vein in slow i.v. bolus dosed within 30 seconds.

Blood samples were collected into $K_2$EDTA tubes over a 48 h period after each treatment at the following time points: predose, 5 min, 10 min, 20 min, 30 min, 45 min, 1 h, 1.5 h, 2 h, 4 h, 6 h, 8 h, 12 h, 24 h and 48 h post administration. Aliquots of plasma were prepared and stored frozen until analysis. Palonosetron concentration in plasma was determined using Liquid chromatography-triple quadrupole mass spectrometry. The lower limit of quantification for palonosetron in dog plasma was 0.02 ng/ml.

Results:

The results are shown in FIG. 1. Palonosetron as ocular drops had a fast absorption comparable to intravenous administration, good systemic exposure and extended elimination phase. The bioavailability was 65.6%. No significant eye irritation was seen.

Experiment 2. Local Tolerance of Palonosetron Formulations in Dog Eye.

Local tolerance of various eye drop formulations in Beagle dogs was evaluated by observing clinical signs continuously during 30 min post dosing. Signs indicating milder ocular discomfort e.g. blepharospasm, pawing the eye, rubbing the face to the floor were recorded descriptively. Summary of the results is presented in the Table 1.

TABLE 1

Signs of milder discomfort (blepharospasm and itching) in dog eye. Number of signs/tested dog when dosing 35 μl/eye.

| Formulation example | 3 mg/ml | | 6 ml/mg | |
|---|---|---|---|---|
| | Blepharospasm | Itching | Blepharospasm | Itching |
| 1 | 9/9 | 9/9 | — | — |
| 3 | 0/15 | 0/15 | 0/12 | 0/12 |
| 4 | 0/2 | 0/2 | — | — |
| 5 | 0/5 | 0/5 | — | — |
| 6 | 1/15 | 2/15 | 0/12 | 0/12 |
| 7 | 7/9 | 2/9 | — | — |
| 8 | 3/5 | 3/5 | — | — |
| 9 | 2/2 | 2/2 | — | — |

The results show that cyclodextrin, in particular hydroxypropyl-β-cyclodextrin, hydroxypropyl-γ-cyclodextrin and sulfobutylether-β-cyclodextrin, significantly improved local tolerance of the eye drop composition by decreasing signs of milder discomfort of the eye such as blepharospasm and itching.

Experiment 3. Efficacy of Palonosetron Eye Drops in Cisplatin-Induced Nausea and Vomiting Model Methods:

Six non-naive adult male Beagle dogs were intravenously administered (2 ml/min) cisplatin at 18 mg/m² body surface over 20 min. Then, 45 min after the end of the infusion, the dogs received eye drops prepared according to Formulation Example 1 at 30 or 120 μg/kg of palonosetron or its vehicle (0.9% saline, 2% povidone) in a cross-over design. Then, the following parameters were recorded by blinded observers over 15 min periods from T0 (end of the infusion of cisplatin) to 420 min (T420) after the end of the infusion of cisplatin: vomiting episodes and nausea-like behaviours including salivation, exaggerated swallowing motions, lip licking, lethargy, restlessness, and turning behaviour signalling that vomiting is imminent. In addition, a visual analogue scale (VAS) from 0 to 100 mm was used to assess the severity of the dogs' nausea-like behaviours (where a score of 0 mm=no nausea and a score of 100 mm=worst possible nausea).

Figure 2:
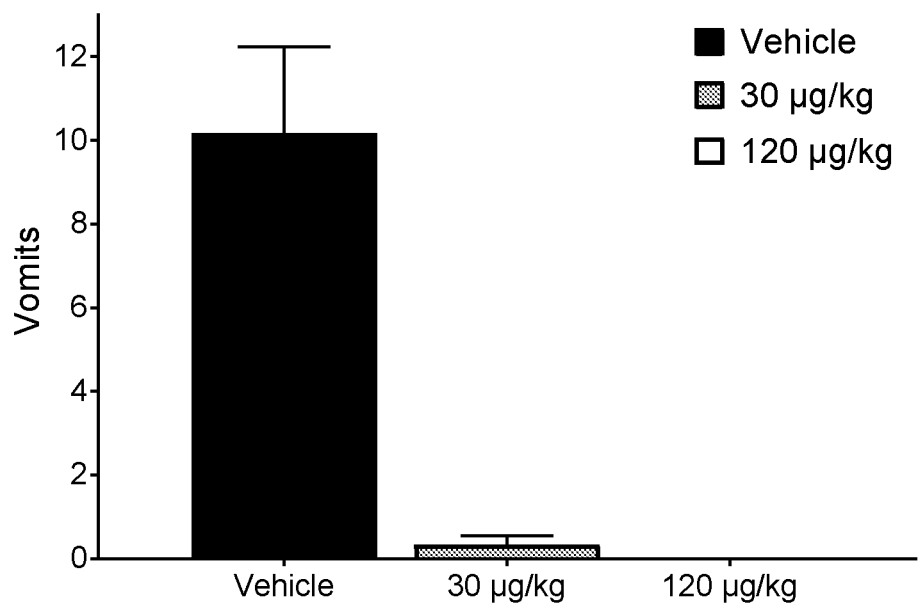
FIG. 2 shows effects of palonosetron 30 and 120 µg/kg eye drops on vomiting after cisplatin 18 mg/m$^2$ exposure in Beagle dogs (n=6). Shown are mean±SEM.

Results:

Effects on Vomiting:

Cisplatin-treated dogs in vehicle eye drops group vomited 10.2±2.1 times (range 5 and 17 times) during the observation period. In palonosetron 30 μg/kg eye drops group, vomiting episodes decreased very strongly with only 1 vomiting episode in 2 dogs overall ($p<0.0001$ vs. vehicle). Palonosetron eye drops at the dose of 120 μg/kg inhibited vomiting totally throughout the observation period ($p<0.0001$). The results are shown in FIG. 2.

Figure 3:
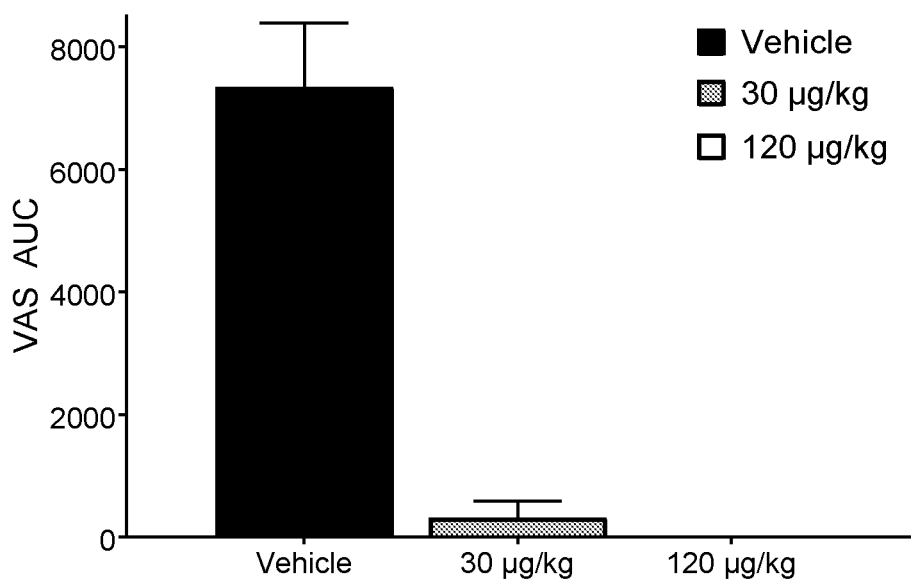
FIG. 3 shows effects of palonosetron 30 and 120 µg/kg eye drops on signs of nausea measured as area under curve (AUC) of visual analog scale (VAS) curve after cisplatin 18 mg/m$^2$ exposure in Beagle dogs (n=6). Shown are mean±SEM.

Effects on Nausea:

In the vehicle-treated group the nausea-associated behaviour started between 2.5 and 2.75 hours after the end of the cisplatin infusion and peaked between 3.75 and 4.25 hours after the end of the cisplatin infusion. The area under the curve (AUC) of VAS was 7344±1050 mm*min in vehicle group. Ocular administration of palonosetron at 30 or 120 μg/kg in cisplatin-treated dogs decreased the VAS score strongly. The VAS AUCs were 320±268 ($p<0.0001$) and 0±0 mm*m ($p<0.0001$) in in 30 μg/kg and 120 μg/kg palonosetron groups, respectively. The results are shown in FIG. 3.

The invention claimed is:

1. A method for the treatment or prevention of nausea and vomiting in a subject comprising administering to the eye of the subject in need thereof an effective amount of an eye drop composition comprising palonosetron or a pharmaceutically acceptable salt thereof as a sole active ingredient.

2. The method according to claim 1, wherein the palonosetron or the pharmaceutically acceptable salt thereof is administered to the eye in an amount ranging from 0.5 μg/kg to 500 μg/kg.

3. The method according to claim 2, wherein the palonosetron or the pharmaceutically acceptable salt thereof is administered to the eye in an amount ranging from 1 μg/kg to 300 μg/kg.

4. The method according to claim 1, wherein the treatment or prevention of nausea and vomiting is associated with chemotherapy-induced nausea and vomiting (CINV), radiotherapy-induced nausea and vomiting (RINV), post-operative nausea, and vomiting (POVN) or motion sickness.

5. The method according to claim 1, wherein the subject to be treated is a human.

6. The method according to claim 1, wherein the subject to be treated is a companion animal chosen from a dog and a cat.

7. The method according to claim 1, wherein the composition comprises:
   (a) 0.01% to 5%, per weight of the composition, of the palonosetron or the pharmaceutically acceptable salt thereof as a sole active ingredient;
   (b) 0.5% to 25% per weight of the composition, of cyclodextrin;
   (c) 0.1% to 10%, per weight of the composition, of a tonicity adjusting agent;
   (d) 0.05% to 5%, per weight of the composition, of a buffering agent; and
   (e) 70% to 99%, per weight of the composition, of sterile water.

8. The method according to claim 7, wherein the tonicity adjusting agent is sodium chloride or mannitol.

9. The method according to claim 7, wherein the cyclodextrin is a member selected from the group consisting of hydroxypropyl-β-cyclodextrin, hydroxypropyl-γ-cyclodextrin and sulfobutylether-β-cyclodextrin.

10. The method according to claim 7, wherein the composition has a pH between 3.5 and 7.0.

11. The method according to claim 10, wherein the composition has a pH between 4.0 and 6.0.

12. The method according to claim 10, wherein the buffering agent is citric acid/sodium citrate.

13. The method according to claim 10, wherein the thickening agent is at least one member selected from the group consisting of polyvinylpyrrolidone, polyvinyl alcohol, polyethylene glycol, polyacrylic acid and a cellulose derivative.

* * * * *